(12) United States Patent
Freiman et al.

(10) Patent No.: US 11,633,118 B2
(45) Date of Patent: Apr. 25, 2023

(54) MACHINE LEARNING SPECTRAL FFR-CT

(71) Applicant: KONINKLIJKE PHILIPS N.V., Eindhoven (NL)

(72) Inventors: Mordechay Pinchas Freiman, Zichron-Yaakov (IL); Liran Goshen, Pardeds-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 443 days.

(21) Appl. No.: 16/498,548

(22) PCT Filed: Jun. 28, 2018

(86) PCT No.: PCT/EP2018/067490
§ 371 (c)(1),
(2) Date: Sep. 27, 2019

(87) PCT Pub. No.: WO2019/002510
PCT Pub. Date: Jan. 3, 2019

(65) Prior Publication Data
US 2020/0113449 A1    Apr. 16, 2020

Related U.S. Application Data

(60) Provisional application No. 62/527,235, filed on Jun. 30, 2017.

(51) Int. Cl.
*A61B 5/026* (2006.01)
*G06N 20/00* (2019.01)
(Continued)

(52) U.S. Cl.
CPC .............. *A61B 5/026* (2013.01); *G06F 30/27* (2020.01); *G06N 20/00* (2019.01); *G06T 5/50* (2013.01);
(Continued)

(58) Field of Classification Search
CPC ....... A61B 5/026; A61B 6/032; A61B 6/4014; A61B 6/405; A61B 6/4241; A61B 6/482;
(Continued)

(56) References Cited

U.S. PATENT DOCUMENTS 7,957,574 B2    6/2011    Sirohey
7,968,853 B2    6/2011    Altman
(Continued)

FOREIGN PATENT DOCUMENTS

| JP | 2015097759 A | 5/2015 |
|---|---|---|
| WO | WO2016001017 A1 | 1/2016 |
| WO | WO2016075331 A2 | 5/2016 |

OTHER PUBLICATIONS

PCT International Search Report, International application No. PCT/EP2018/067490, dated Nov. 16, 2018.
(Continued)

*Primary Examiner* — Manuchehr Rahmjoo
(74) *Attorney, Agent, or Firm* — Larry Liberchuk

(57) ABSTRACT

A system (100) includes a computer readable storage medium (122) with computer executable instructions (124), including: a biophysical simulator (126) configured to determine a fractional flow reserve value. The system further includes a processor (120) configured to execute the biophysical simulator (126), which employs machine learning to determine the fractional flow reserve value with spectral volumetric image data. The system further includes a display configured to display the determine fractional flow reserve value.

15 Claims, 2 Drawing Sheets

(51) Int. Cl.
 G06F 30/27 (2020.01)
 G06T 5/50 (2006.01)
 G06T 7/00 (2017.01)
(52) U.S. Cl.
 CPC .. G06T 7/0012 (2013.01); *G06T 2207/10081* (2013.01); *G06T 2207/30104* (2013.01)
(58) Field of Classification Search
 CPC ....... A61B 6/504; A61B 6/5217; G06F 30/27; G06N 20/00; G06T 2207/10081; G06T 2207/30104; G06T 5/50; G06T 7/0012; G16H 30/40; G16H 50/50; G16H 50/70
 See application file for complete search history.

(56) References Cited

U.S. PATENT DOCUMENTS

| | | | |
|---|---|---|---|
| 9,788,807 B2 | 10/2017 | Schmitt | |
| 10,010,255 B2* | 7/2018 | Fonte | A61B 5/021 |
| 10,210,612 B2 | 2/2019 | Gulsun | |
| 10,258,303 B2 | 4/2019 | Grass | |
| 10,769,780 B2 | 9/2020 | Freiman | |
| 10,888,234 B2 | 1/2021 | Sharma | |
| 10,970,836 B2 | 4/2021 | Lamash | |
| 11,087,884 B2 | 8/2021 | Sankaran | |
| 11,298,187 B2 | 4/2022 | Taylor | |
| 11,557,069 B2 | 1/2023 | Senzig | |
| 2015/0112182 A1* | 4/2015 | Sharma | A61B 5/7264 600/408 |
| 2015/0282765 A1 | 10/2015 | Goshen | |
| 2015/0297161 A1 | 10/2015 | Grass | |
| 2016/0148371 A1 | 5/2016 | Itu | |
| 2016/0302750 A1 | 10/2016 | Nickisch | |
| 2017/0076062 A1 | 3/2017 | Choi | |
| 2017/0095292 A1 | 4/2017 | Taylor | |

OTHER PUBLICATIONS

Freiman M. et al., "Learning an Optimal Database for Patch-Based Medical Image Segmentation: A Total-Variation Approach", Electrical Engineering and Systems Science, Image and Video Processing, Jun. 2019.
Freiman M. et al., "Improving CCTA-Based Lesions' Hemodynamic Significance Assessment by Accounting for Partial Volume Modeling in Automatic Coronary Lumen Segmentation", Medical Physics, vol. 44, issue 3, pp. 1040-1049, 2017.
Freiman et al., "Automatic Coronary Lumen Segmentation with Partial Volume Modeling Improves Lesions' Hemodynamic Significance Assessment", Progress in Biomedical Optics and Imaging—Proceedings of SPIE, vol. 9784, 2016.
Vorobtsova N. et al., "Effects of Vessel Tortuosity on Coronary Hemodynamics: An Idealized and Patient-Specific Computational Study", Annals of Biomedical Engineering, vol. 44, No. 7, pp. 2228-2239, Jul. 2016.
Lee M.S et al., "Myocardial Bridging: An Up-to-Date Review", The Journal of Invasive Cardiology, vol. 27, No. 11, pp. 521-528, Nov. 2015.
Meijboom W. B. et al., "Comprehensive Assessment of Coronary Artery Stenoses. Computed Tomography Coronary Angiography Versus Conventional Coronary Angiography and Correlation With Fractional Flow Reserve in Patients With Stable Angina", Journal of the American College of Cardiology., vol. 52, No. 8, pp. 636-643, 2008.
Coenen A. et al., "Fractional Flow Reserve Computed from Noninvasive CT Angiography Data: Diagnostic Performance of an On-Site Clinician-Operated Computational Fluid Dynamics Algorithm", Radiology, vol. 274, No. 3, pp. 674-683, Mar. 2015.
Norgaard B. L. et al., "Diagnostic Performance of Non-Invasive Fractional Flow Reserve Derived from Coronary CT Angiography in Suspected Coronary Artery Disease: The NXT Trial", Journal of the American College of Cardiology, vol. 63, No. 12, pp. 1145-1155, 2014.
Nickisch H. et al.,"Learning Patient-Specific Lumped Models for Interactive Coronary Blood Flow Simulations," in Medical Image Computing and Computer-Assisted Intervention—MICCAI 2015: 18th International Conference, LNCS, vol. 9350, pp. 433-441, 2015.
Murray C. J. L. et al., "Global, Regional, and National Age-Sex Specific All-Cause and Cause-Specific Mortality for 240 Causes of Death, 1990-2013: A Systematic Analysis for the Global Burden of Disease Study 2013", GBD 2015 Mortality and Causes of Death Collaborators, Lancet, vol. 385, No. 9963, pp. 117-171, 2015.
Danad I. et al., "Dual-Energy Computed Tomography for Detection of Coronary Artery Disease", Expert Rev. Cardiovasc. Ther., vol. 13, No. 12, pp. 1345-1356, Dec. 2015.
Williams M.C. et al., "CT Coronary Angiography in Patients with Suspected Angina Due to Coronary Heart Disease (SCOT-HEART): An Open-Label, Parallel-Group, Multicentre Trial", Lancet, vol. 385, No. 9985, pp. 2383-2391, 2015.
Lugauer F. et al.,"Precise Lumen Segmentation in Coronary Computed Tomography Angiography", International MICCAI Workshop on Medical Computer Vision MCV 2014: Medical Computer Vision: Algorithms for Big Data, vol. 8848, pp. 137-147, 2014.
Wustmann K. et al., "Is There Functional Collateral Flow During Vascular Occlusion in Angiographically Normal Coronary Arteries?", Circulation, vol. 107, No. 17, pp. 2213-2220, 2003.
Taylor C. A. et al., "Computational Fluid Dynamics Applied to Cardiac Computed Tomography for Noninvasive Quantification of Fractional Flow Reserve: Scientific Basis", Journal of the American College of Cardiology, vol. 61, No. 22, pp. 2233-2241, Jun. 2013.
Itu L. et al., "A Machine-Learning Approach for Computation of Fractional Flow Reserve from Coronary Computed Tomography", Journal of Applied Physiological Society, vol. 121, No. 1, pp. 42-52, 2016.
Hart P.E. et al., "Nearest Neighbor Pattern Classification," IEEE Transactions on Information Theory, vol. 13, Issue 1, pp. 21-27, Jan. 1967.
Powell M.J.D. et al., "The BOBYQA Algorithm for Bound Constrained Optimization Without Derivatives", NA Rep. NA2009/06. 39, 2009.
Comaniciu D. et al., "Shaping the Future Through Innovations: From Medical Imaging to Precision Medicine", Medical Image Analysis, vol. 33, pp. 19-26, Oct. 12, 2016.
Min J.K. et al., "Noninvasive Fractional Flow Reserve Derived from Coronary CT Angiography", The American College of Cardiology Foundation, Cardiovascular Imaging, vol. 8, No. 10, pp. 1213-1222, Oct. 2015.

* cited by examiner

MACHINE LEARNING SPECTRAL FFR-CT

FIELD OF THE INVENTION

The following generally relates to imaging and more particularly to determining fractional flow reserve (FFR) estimates from spectral image data, and is described with particular application to computed tomography (CT).

BACKGROUND OF THE INVENTION

Fractional flow reserve (FFR) is an invasive measure in the catheterization laboratory (Cath Lab) to quantify, via an FFR index, the hemodynamic significance of a coronary lesion due to calcified or soft plaque. The index indicates the functional severity of a coronary stenosis that is calculated from pressure measurements made during coronary arteriography and is defined as the distal blood pressure (behind a stenosis) relative to the proximal pressure (close to the ostium) under hyperemic conditions. That is, the FFR index expresses the maximal flow down a vessel in the presence of a stenosis compared to the maximal flow in the hypothetical absence of the stenosis. The FFR value is an absolute number between 0 and 1, where a value 0.50 indicates that a given stenosis causes a 50% drop in blood pressure.

The FFR invasive procedure requires insertion of a catheter into the femoral or radial arteries and advancement of the catheter to the stenosis where a sensor at the tip of the catheter senses pressure, temperature, and flow across the stenosis, during conditions promoted by various agents that effect vessel geometry, compliance and resistance, and/or other characteristics. FFR-CT is non-invasive imaging approach to estimate an FFR index from CT image data of the heart (e.g., from coronary computed tomography angiography, CCTA). This includes: (1) computational fluid dynamic (CFD); (2) lumped model (LM), and (3) machine learning (ML) approaches.

The ML approach has been used to learn a statistical model associates input features derived from conventional CT data and flow-related parameters at each coronary location using a machine-learning engine. An example is described in Itu, et al., "A machine-learning approach for computation of fractional flow reserve from coronary computed tomography.," J. Appl. Physiol., vol. 121, no. 1, pp. 42-52, 2016. This approach relies upon input CCTA image. Unfortunately, CCTA image data can be limited in accurately characterizing underlying anatomy and physiology of a patient. An example of such a limitation is over-estimating of myocardial perfusion deficit, e.g., due to beam hardening. Another example of such a limitation is underestimating of a lumen radius, e.g., due to calcium blooming.

SUMMARY OF THE INVENTION

Aspects described herein address the above-referenced problems and others.

Described herein is an approach to estimate fractional flow reserve (FFR) estimates from spectral coronary computed tomography angiography (sCCTA) by combining spectral volumetric image data (e.g., CT) with a machine-learning (ML) engine to estimate the FFR values along the coronary tree. The approach uses spectral volumetric image data along with spectrally enhanced image analysis methods applied to the sCCTA data to derive a set of features served as input to a machine-learning model trained to predict flow related parameters for the coronary tree.

In one aspect, a system includes a computer readable storage medium with computer executable instructions, which includes a biophysical simulator configured to determine a fractional flow reserve value. The system further includes a processor configured to execute the biophysical simulator, which employs machine learning to determine the fractional flow reserve value with spectral volumetric image data. The system further includes a display configured to display the determined fractional flow reserve value.

In another aspect, a computer readable medium is encoded with computer executable instructions which when executed by a processor causes the processor to: receive spectral volumetric image data, process the spectral volumetric image data with a machine learning engine to determine a fractional flow reserve index, and visually present the fractional flow reserve index.

In another aspect, a method includes receiving spectral volumetric image data, processing the spectral volumetric image data with a machine learning engine to determine a fractional flow reserve index, and visually presenting the fractional flow reserve index.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
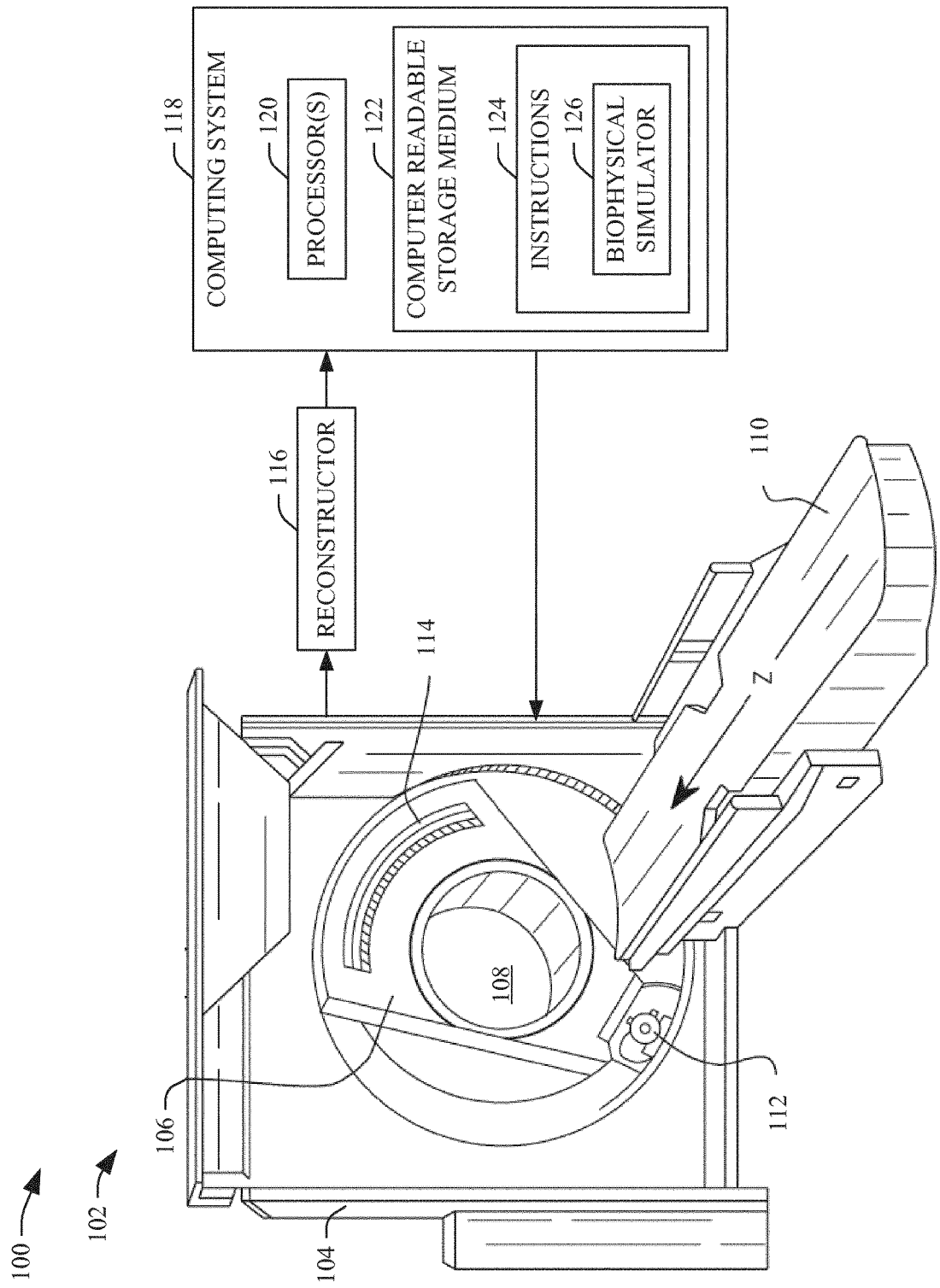
FIG. 1 schematically illustrates a system, including a computing system, with a biophysical simulator, and an imaging system.

FIG. 1 schematically illustrates a system 100 including an imaging system 102 such as a CT scanner configured for spectral (multi-energy) imaging. The imaging system 102 includes a generally stationary gantry 104 and a rotating gantry 106, which is rotatably supported by the stationary gantry 104 and rotates around an examination region 108 about a z-axis. A subject support 110, such as a couch, supports an object or subject in the examination region 108.

A radiation source 112, such as an x-ray tube, is rotatably supported by the rotating gantry 106, rotates with the rotating gantry 106, and emits radiation that traverses the examination region 108. In one instance, the radiation source 112 includes a single broad spectrum x-ray tube. In another instance, the radiation source 112 includes a single x-ray tube configured to switch between at least two different emission voltages (e.g., 80 kVp and 140 kVp) during scanning. In yet another instance, the radiation source 112 includes two or more x-ray tubes configured to emit radiation having different mean spectra. In still another instance, the radiation source 112 includes a combination thereof.

A radiation sensitive detector array 114 subtends an angular arc opposite the radiation source 112 across the examination region 108. The radiation sensitive detector array 114 detects radiation traversing the examination region 108 and generates an electrical signal(s) (projection data) indicative thereof. Where the radiation source 112 includes a single broad spectrum x-ray tube, the radiation sensitive detector array 112 includes energy-resolving detectors (e.g., direct conversion photon counting detectors, at least two sets of scintillators with different spectral sensitivities (multi-layer), etc.). With kVp switching and multi-tube configurations, the detector array 114 can include single layer detectors, direct conversion photon counting detectors, and/or multi-layer detectors. The direct conversion photon counting detectors may include a conversion material such as CdTe, CdZnTe, Si, Ge, GaAs, or other direct conversion material. An example of multi-layer detector includes a double decker detector such as the double decker detector described in U.S. Pat. No. 7,968,853 B2, filed Apr. 10, 2006, and entitled "Double Decker Detector for Spectral CT," the entirety of which is incorporated herein by reference.

A reconstructor 116 receives spectral projection data from the detector array 114 and reconstructs spectral volumetric image data such as sCCTA image data, a high-energy image, a low energy image, a photoelectric image, a Compton scatter image, an iodine image, a calcium image, a virtual non-contrast image, a bone image, a soft tissue image, and/or other basis material image. The reconstructor 116 can also reconstruct non-spectral volumetric image data, e.g., by combining spectral projection data and/or spectral volumetric image data. Generally, the spectral projection data and/or spectral volumetric image data will include data for at least two different energies and/or energy ranges.

A computing system 118 serves as an operator console. The console 118 includes a human readable output device such as a monitor and an input device such as a keyboard, mouse, etc. Software resident on the console 118 allows the operator to interact with and/or operate the scanner 102 via a graphical user interface (GUI) or otherwise. The console 118 further includes a processor 120 (e.g., a microprocessor, a controller, a central processing unit, etc.) and a computer readable storage medium 122, which excludes non-transitory medium, and includes transitory medium such as a physical memory device, etc. The computer readable storage medium 122 includes instructions 124 for at least a biophysical simulator 126. The processor 120 is configured to execute the instructions 124. The processor 120 may additionally be configured to execute one or more computer readable instructions carried by a carrier wave, a signal and/or other transitory medium. In a variation, the processor 120 and the computer readable storage medium 122 are part of another computing system, which is separate from the computing system 118.

The biophysical simulator 126 is configured to process at least the spectral volumetric image data generated by the reconstructor 116 and/or other imaging system to perform a biophysical simulation. With respect to FFR, the biophysical simulator determines an FFR index therefrom. As described in greater detail below, the biophysical simulator 126 estimates a fractional flow reserve (FFR) index from spectral volumetric image data using a machine-learning engine. This approach does not employ flow simulation to determine FFR values. Generally, the approach uses a spectrally enhanced image analysis approach to derive a set of features which is used as input to a machine-learning (ML) model trained to predict flow related parameters for the coronary tree. This approach may mitigate artifact associated with non-spectral techniques, including beam hardening, calcium blooming, etc., which may introduce bias in accurately predicting the patient-specific flow measurements.

Figure 2:
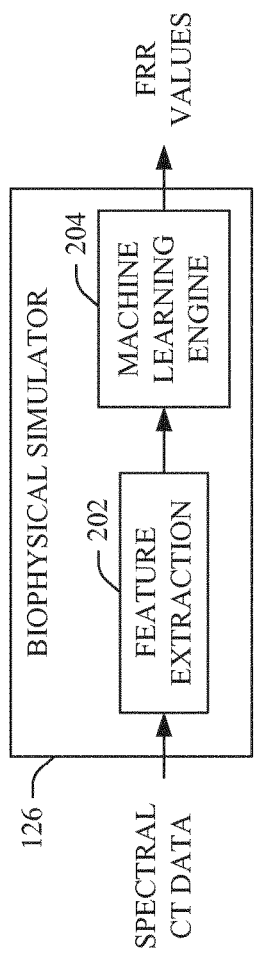
FIG. 2 schematically illustrates an example of the biophysical simulator.

FIG. 2 schematically illustrates an example of the biophysical simulator 126.

A feature extraction component 202 receives, as input, spectral volumetric image data generated by the imaging system 102 and/or other spectral imaging system. The feature extraction component 202 extracts features from the spectral volumetric image data. The features can be divided into multiple groups, such as, but not limited to: (1) spectrally enhanced anatomical features; (2) spectrally enhanced plaque morphological and functional features, and (3) spectrally enhanced physiological features. Each of these features are described in greater detail below.

Spectrally enhanced anatomical features.

This group of features include, but is not limited to, geometrical and topological features of the coronary tree. Geometrical features can include lumen radius at each location, upstream and downstream lumen radius and stenosis, inlet and outlet radiuses, etc. These features can be derived from a spectrally enhanced 3-D model of the coronary tree generated from data with automatic algorithms and/or adjusted manually using various tools. An automatic algorithm example is discussed in Freiman, et al., "Automatic coronary lumen segmentation with partial volume modeling improves lesions' hemodynamic significance assessment," in Progress in Biomedical Optics and Imaging—Proceedings of SPIE, 2016, vol. 9784. The feature extraction component 202 leverages the spectral volumetric image data to enhance the segmentation.

Additional anatomical features include a level of coronary tortuosity, which can influence the flow of blood through the coronary artery due to constriction of the artery while the heart muscle squeezes (an example is discussed in Vorobtsova et al., "Effects of Vessel Tortuosity on Coronary Hemodynamics: An Idealized and Patient-Specific Computational Study," Ann. Biomed. Eng., vol. 44, no. 7, pp. 2228-2239, 2016) and/or a presence and a length of myocardial bridge associated with elastin degeneration, which may imply increased coronary stiffness (an example is discussed in Lee, et al., "Myocardial Bridging: An Up-to-Date Review," J. Invasive Cardiol., vol. 27, no. 11, pp. 521-8, 2015). Topological features can consist of a number of branches, branching level for each point, etc.

Examples of enhancement include: (1) using different spectral results to determine the presence of different components of the coronary tree anatomy, e.g., use of an iodine map to determine the presence of the lumen and virtual non-contrast image or z-effective map to determine the presence of calcified plaque; (2) using different mono-energetic images to find the boundary between different components rather than a single conventional image for the entire segmentation task, e.g., use of low mono-energetic images to define the boundary between lumen and soft-plaque and high mono-energetic images to separate between calcified plaque and iodine in the lumen; and (3) using a spectrally enabled regularization to improve segmentation quality.

Examples of regularization include but are not limited to: (1) regularization over the different spectral results; and (2) regularization over the materials domain. The following provides an example in which spectral information is incorporated into an automatic coronary tree segmentation framework. In this example, the coronary lumen segmentation is formulated as a maximum a posterior estimation problem involves two terms: (1) a spectral data term; and (2) a spectral regularization term. It is to be appreciated that other formulations are contemplated herein, and the below formulation is not limiting.

The spectral data term represents a likelihood of that each 3-D point belongs to one of the following classes: coronary lumen, calcified plaque, soft plaque, background. An example of a spectral data term is shown in Equation 1:

$$\varphi_c(x,c_i)=Pr(f_{SCT}(x)\in c_i), \quad \text{Equation 1:}$$

where x is a 3-D point, $c_i$ is an ith class to be assigned to x, Pr( ) represents a probability, and $f_{SCT}(x)$ extracts spectrally-enabled features from the spectral volumetric image data, e.g., iodine and calcium maps, and $Pr(f_{SCT}(x)\in c_i)$ represents a statistical model that describes a relationship between spectral features and the different classes.

The spectral regularization term penalizes neighboring points assigned to different classes (e.g., lumen/background). A general example of a regularization term is shown in Equation 2:

$$\omega(x_1, x_2)=Pr(x_1\in c_1 \wedge x_2 \notin c_1). \quad \text{Equation 2:}$$

An example of a spectral regularization term or a spectrally enabled regularization term is shown in Equation 3:

$$\varphi_c(x, c_i) = Pr(x_1 \in c_1 \wedge x_2 \notin c_1) = \exp\left(-\frac{(f_s(x_1) - f_s(x_2))^2}{\sigma_s^2}\right), \quad \text{Equation 3}$$

where $f_s(x)$ is a feature-vector derived at point x from the spectral volumetric data, and $\sigma_s^2$ is an expected in-class variance over the spectral feature-vectors. A set of features by means of geometrically related quantities derived from the patient's spectrally enhanced 3D model of the coronary tree potentially related to the coronary blood flow can be defined as: patient_spectral_features.

Spectrally enhanced plaque morphological and functional features.

In this example, the feature extraction component 202 extracts features from the spectral volumetric data as quantities derived from the patient's cardiac volumetric image data potentially related to the coronary blood flow. Features extracted from non-spectral volumetric image data and how to utilize them to derive a personalized boundary condition model are described in patent application s/n EP14174891.3, filed Jun. 30, 2014, and entitled "Enhanced Patient's Specific Modelling For FFR-CT," patent application Ser. No. U.S. 62/251,417, filed Nov. 5, 2015, and entitled "Collateral Flow Modelling For FFR-CT," which are incorporated herein by reference in their entireties.

The output of feature extraction component 202 for these features includes, e.g.: (1) spectral plaque morphological features, where plaque is detected, segmented and classified using spectral results, e.g., a calcium map with no soft tissue, a calcium map with no iodine, etc.; (2) spectral plaque functional features, where the plaque decomposition is characterized based upon spectral results, e.g., a calcium map with no soft tissue, a calcium map with no iodine, etc.; and/or (3) other features. The quantities derived from the spectrally enabled plaque morphological and functional characterization can be also defined as: patient_spectral_features.

Spectrally enhanced physiological features.

Physiological features extracted from the spectral volumetric data are quantities derived from the patient's cardiac volumetric image data potentially related to the coronary blood flow. The output of feature extraction component 202 for these features predict more accurately and precisely FFR values. These features can include but not limited to: (1) spectral myocardium deficits, where the myocardium deficits are detected, segment and assessed using spectral results, e.g., iodine map; (2) spectral collateral flow, where the collateral flow estimate is enhanced by spectral results, e.g., iodine map, and/or (3) other features.

For myocardium deficits, the patient_spectral_features$\in R^n$ is a feature vector that describes spectrally determined perfusion deficit features. These features can be derived from spectral volumetric image data and include the iodine map, beam-hardening corrected mono energetic images, etc. The personalization function (patient_spectral_features): $R^n \to R$ defines a relationship between the spectrally enabled perfusion deficit features and the scaling of the global resistance.

Assessment of collateral flow from the spectral volumetric image data can be done for example by the following steps: (1) determine the coronary tree, including lumen and wall, as described herein and/or other approach; (2) determine a myocardium feeding territory of each coronary, e.g., by using Voronoi diagrams and/or other approach; and (3) quantify a presence of collateral flow, e.g., by determining additional iodine-related enhancement in the feeding territory of a coronary artery that is not related to the flow through the coronary. The term patient_spectral_features$\in R^n$ is a feature vector that describes spectrally determined collateral flow features.

A machine learning (ML) engine 204 maps the patient_spectral_features onto FFR values: $f(\text{patient\_spectral\_features}) \to FFR$. The function can be used to estimate the FFR value at each location of the coronary tree by calculating the input features describing the specific location at the coronary tree and apply the function $f$ on this input. The function $f$ describes implicitly the statistical relation between the input features and the output FFR values. Several machine-learning models can be used to find the function $f$ using a supervised-learning methodology. Generally, the ML engine 204 uses the function $f$ to predict FFR values non-invasively from features extracted from the spectral volumetric image data, where the features describe patient specific anatomy and physiology and are extracted from the spectral volumetric image data.

Figure 3:
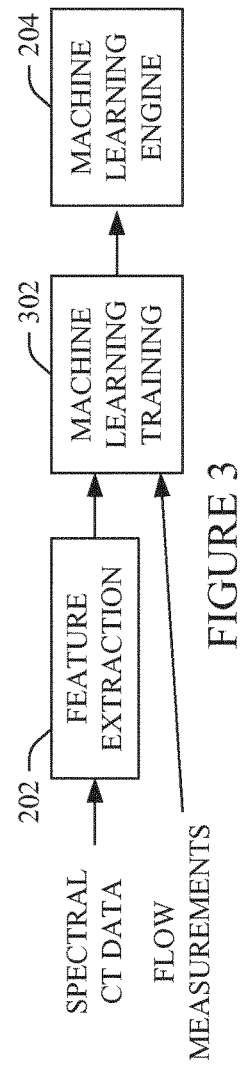
FIG. 3 illustrates an example training system for the biophysical simulator.

In this example, multiple pairs of input and outputs known as the training data are used to find f using some optimization criteria. Examples for approaches to describe and find f include but are not limited to: (1) deep neural networks; (2) regression forests; (3) random forests; (4) support vector machines, and/or (5) other approaches. A suitable training system is shown in FIG. 3, which includes the feature extraction component 202, a machine learning training component 302, and the machine learning engine 204. A suitable training procedure is shown in Equation 4:

$$\hat{f} = \underset{f}{\arg\min} \text{Error}(f(\text{patient\_spectral\_featuers}), FFR_{GT}) \quad \text{Equation 4}$$

where $f$ is the function mapping the input features onto the FFR values, patient_spectral_features, are the spectrally enhanced features computed as described herein, $FFR_{GT}$ are the expected output values of the function $f$, and Error is the machine-learning model that is used. In some models, a regularization term is included explicitly in Error, and in others regularization to avoid over-fitting to the training data can be achieved using standard techniques, such as cross-validation. Optimization can be done using the stochastic gradient decent algorithm, among others.

Generally, the ML engine 204 is trained by a set of spectral volumetric image data and associated flow measurements to learn a statistical model that connects the spectral volumetric image data and flow measurements. The training data includes data with known results. The statistical model implicitly describes the association between the input features and the output flow parameters. It accounts for potential biases in ML based flow prediction based upon non-spectral volumetric image data, by providing more detailed and accurate characterization of the underlying anatomy and physiology to derive from the input features to the ML model.

The approach described herein, in one instance, provides an improved noninvasive, accurate, objective assessment of coronary lesions' hemodynamic significance by means of fractional flow reserve (FFR). The approach enables coronary fast characterization of lesions hemodynamic significance based on data from spectral volumetric image data, which, in one instance, better characterize the anatomy and physiology of the patient, relative to non-spectral image data, and has the potential to provide more accurate FFR estimates, and an ML engine that does not requires explicit assignment of boundary condition and heavy computations.

The following describes a machine learning algorithm to improve automatic coronary lumen segmentation. In one instance, this is achieved by selecting a subset of prototypes from a given database so that the classification performance for any new sample will be as accurate as possible. In one example, the subsampled database represents the full structure of the population with as few prototypes as possible.

Prototypes are ranked in the original database according to their location on the manifold. For this example, a prototype is located in a center of its class when its neighboring prototypes, according to some pre-defined metric, are of the same class, and as located on the boundary between classes if it has many neighbors from different classes. For a prototype feature-vector $\vec{x}_p$, an example classification rank $R(\vec{x}_p)$ is shown in Equation 5:

$$R(\vec{x_p}) = \frac{\sum_{k=1}^{K} 1 - \delta(C(\vec{x_p}), C(\vec{x_k}))}{\sum_{k=1}^{K} \delta(C(\vec{x_p}), C(\vec{x_k}))}, \quad \text{Equation 5}$$

where K is a number of neighbors around $\vec{x}_p$, $C(\vec{x}_p)$ is a class of $\vec{x}_p$, $\vec{x}_k$ is a neighbor of $\vec{x}_p$, and $$\delta(C(\vec{x_p}), C(\vec{x_k})) = \begin{cases} 1, & C(\vec{x_p}) = C(\vec{x_k}) \\ 0, & C(\vec{x_p}) \neq C(\vec{x_k}) \end{cases}.$$

According to this definition, $R(\vec{x}_p)$ will have a high value when the prototype $\vec{x}_p$ has many neighboring prototypes from other classes, and a low value when the prototype $\vec{x}_p$ has many neighboring prototypes from its own class.

The distribution of the classification ranks of the prototypes in the original database for each class can be described using a histogram with N bins. Each bin contains 100/N percent of the prototypes in the original database. A sampled database can be defined as a function of the percentile of prototypes to be selected from each bin of the histogram: $DB(\vec{N})$, where $\vec{N}$ is the vector of the percentiles for each bin. Given the function $DB(\vec{N})$ to sample the original database, a functional is defined to estimate the parameters N. In one instance, the estimate maximizes the capability of the sampled database to correctly classify each sample while minimizing the overall number of samples. In one instance, this is achieved while rendering the classification robust to small variations in the samples.

An example functional is shown in Equation 6:

$$E_{\alpha,\beta}(\vec{N}) = TV(\vec{N}) + \alpha f(c(\vec{x}) - u_{DB(\vec{N})}(\vec{x}))^2 + \beta \|DB(\vec{N})\|, \quad \text{Equation: 6}$$

Wherein $DB(\vec{N})$ is the sampled database constructed form the original database by sampling the different bins according to the percentiles specified at $\vec{N}$, $u_{DB(\vec{N})}(\vec{x})$ is the classification of the patch using the sampled database $DB(\vec{N})$, $\|DB(\vec{N})\|$ is the number of the patches in the sampled database $DB(\vec{N})$, $\alpha$, $\beta$ are weighting meta-parameters controlling the contribution of each term, and $TV(\vec{N})$ measure a difference in the classification of each patch in $DB(\vec{N})$ to small variation in its appearance (where TV=total-variation). An example is shown in Equation 7:

$$TV(\vec{N}) = \sum_{\vec{x} \in DB(\vec{N})} \sum_{j=0}^{J} \left| u_{DB(\vec{N})}(\vec{x}) - u_{DB(\vec{N})}(\vec{x} + \vec{h}_j) \right|, \quad \text{Equation: 7}$$

where J is the dimension of the patch $\vec{x}$, and $\vec{h}_j$ is the vector of the same dimension with zeros at all entries except at entry j, and $|u_{DB(\vec{N})}(\vec{x}) - u_{DB(\vec{N})}(\vec{x} + \vec{h}_j)|$ is the absolute difference between the classification of $\vec{x}$ and $\vec{x} + \vec{h}_j$ given the database $DB(\vec{N})$. Optimal database sampling parameters can be found by minimizing the energy functional an example is shown in Equation 8:

$$\hat{\vec{N}} = \operatorname*{argmin}_{\vec{N}} E_{\alpha,\beta}(\vec{N}), \quad \text{Equation: 8}$$

where the hyper-parameters $\alpha, \beta$ can be either adjusted manually or learned using a numerical optimization process adapted for a specific task.

The above can be utilized to reduce the database size required for the coronary lumen segmentation algorithm. As example coronary lumen segmentation algorithm is described in Freiman et al., "Improving CCTA-based lesions' hemodynamic significance assessment by accounting for partial volume modeling in automatic coronary lumen segmentation," Med. Phys. 44, 1040-1049 (2017). The algorithm formulates the segmentation task as an energy minimization problem over a cylindrical coordinate system, where the warped volume along the coronary artery centerline is expressed with the coordinate i representing the index of the cross-sectional plane, and θ, r represent the angle and the radial distance determining a point in the cross-sectional plane.

As example is shown in Equation 9:

$$E(X) = \sum_{p \in P} \psi_p(x_p) + \lambda \sum_{p,q \in E} \psi_{p,q}(x_p, x_q),$$  Equation 9 where P is the set of sampled points, $x_p$ is a vertex in the graph representing the point ($i^{x_p}$, $\theta^{x_p}$, $r^{x_p}$) sampled from the original CCTA volume, $\psi_p(x_p)$ represents the likelihood of the vertex to belong to the lumen or the background class, p, q are neighboring vertices according to the employed neighboring system E, and $\psi_{p,q}(x_p, x_q)$ is a penalty for neighboring vertices belonging to different classes ensure the smoothness of the resulted surface.

The algorithm calculates the likelihood of each vertex $x_p$ belonging to the coronary lumen from a large training database with rays sampled from cardiac CTA data along with manually edited lumen boundary location represented as a binary rays serving as the database prototypes. This can be based on the KNN algorithm described in Hart et al., "Nearest neighbor pattern classification," IEEE Trans. Inf. Theory. 13, 21-27 (1967). The likelihood term is additionally adjusted to account for partial volume effects and a L2 norm used as the regularization term as described in Freiman et al.

The following provides an application of the database optimization. Considering lumen radiuses as a different class of the rays, the functional hyper-parameters are optimized to achieve a maximal area under the curve (AUC) for CT-FFR estimates with the segmentations obtained using the optimized database with invasive FFR measurements as the reference. For a two-phase optimization task, an outer loop optimizes the model hyper-parameters $\alpha, \beta$ as shown in Equation 10:

$$\widehat{\alpha, \beta} = \underset{\alpha, \beta}{\mathrm{argmax}} AUC\big(FFR_{CT}\big(DB(\vec{N})\big), FFR_{GT}\big),$$  Equation 10 and an inner loop finds the optimal model parameters for given $\alpha, \beta$ using Equation 8. The optimization can be carried out using a derivative-free Bound Optimization BY Quadratic Approximation (BOBYQA) algorithm. An example of such an algorithm is discussed in Powell, "The BOBYQA algorithm for bound constrained optimization without derivatives," NA Rep. NA2009/06. 39 (2009).

Figure 4:
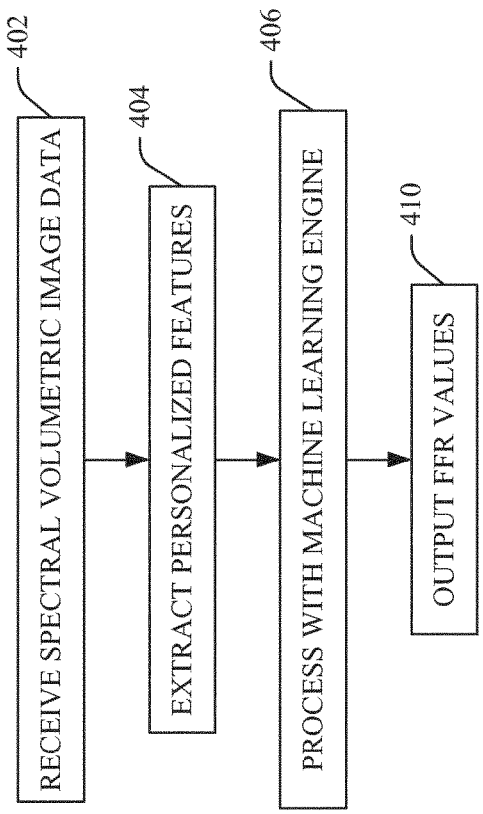
FIG. 4 illustrates an example method in accordance with an embodiment herein.

FIG. 4 illustrates an example method in accordance with an embodiment described herein.

It is to be appreciated that the ordering of the above acts is not limiting. As such, other orderings are contemplated herein. In addition, one or more acts may be omitted and/or one or more additional acts may be included.

At 402, spectral volumetric image data is received, as described herein and/or otherwise.

At 404, features are extracted from the spectral volumetric image data, as described herein and/or otherwise.

At 408, the extracted features are processed with a machine learning algorithm to estimate FFR values, as described herein and/or otherwise.

At 410, the FFR values are output.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system, comprising:
    a memory that stores a plurality of instructions;
    processor circuitry configured to carry out the plurality of instructions to execute a machine learning engine configured to map spectrally enhanced features extracted from spectral computed tomography (CT) volumetric image data onto fractional flow reserve (FFR) values to determine the FFR value with spectral volumetric image data, wherein the spectral CT volumetric image data include data for at least two different energies and/or energy ranges; and
    a display configured to visually present the determined FFR value.

2. The system of claim 1, wherein the processor circuitry is further configured to extract a feature from the spectral CT volumetric image data, wherein the extracted feature includes at least one of a spectrally enhanced anatomical feature, a spectrally enhanced plaque morphological and functional feature, and a spectrally enhanced physiological feature.

3. The system of claim 2, wherein the spectrally enhanced anatomical feature includes a geometrical and topological feature.

4. The system of claim 3, wherein the processor circuitry is further configured to enhance an anatomical feature using different spectral images to determine a presence of different anatomical tissue of a coronary tree anatomy.

5. The system of claim 3, wherein the processor circuitry is further configured to enhance an anatomical feature using different mono-energetic images to find a boundary between different anatomical tissue of a coronary tree anatomy.

6. The system of claim 3, wherein the processor circuitry is further configured to enhance an anatomical feature using spectrally enabled regularization.

7. The system of claim 2, wherein the processor circuitry is further configured to extract a spectral morphological feature by detecting, segmenting and classifying using the spectral volumetric image data.

8. The system of claim 2, wherein the spectrally enhanced physiological feature includes a quantity related to coronary blood flow.

9. The system of claim 8, wherein the spectrally enhanced physiological feature includes one or more of a spectral myocardium deficit or a spectral collateral flow.

10. The system of claim 1, wherein the machine learning engine estimates the FFR value at a predetermined location of a coronary tree by applying a function on a feature describing the predetermined location.

11. The system of claim 10, wherein the function describes a statistical relationship between the feature and the FFR value.

12. A non-transitory computer readable medium having one or more executable instructions stored thereon, which when executed by processor circuitry, cause the processor circuitry to:
  receive spectral computed tomography (CT) volumetric image data, wherein the spectral CT volumetric image data include data for at least two different energies and/or energy ranges;
  process the spectral CT volumetric image data with a machine learning engine configured to map spectrally enhanced features extracted from the spectral CT volumetric image data onto fractional flow reserve (FFR) values to determine a FFR value; and
  visually present the FFR value.

13. The non-transitory computer readable medium of claim 12, wherein the machine learning engine estimates the FFR value at a predetermined location of a coronary tree by applying a function on a feature describing the predetermined location.

14. The non-transitory computer readable medium of claim 13, wherein the function describes a statistical relationship between the feature and the FFR value.

15. A computer-implemented method, comprising:
  receiving spectral computed tomography (CT) volumetric image data, wherein the spectral CT volumetric image data include data for at least two different energies and/or energy ranges;
  processing the spectral CT volumetric image data with a machine learning engine configured to map spectrally enhanced features extracted from the spectral CT volumetric image data onto fractional flow reserve (FFR) values;
  estimate an FFR value at a predetermined location of a coronary tree by applying a function on a feature describing the predetermined location, wherein the function describes a statistical relationship between the feature and the FFR value; and
  visually presenting the FFR value.

* * * * *